US007799318B2

(12) United States Patent
Esposito et al.

(10) Patent No.: US 7,799,318 B2
(45) Date of Patent: *Sep. 21, 2010

(54) LIQUID STICK ANTIPERSPIRANT

(75) Inventors: Anthony Esposito, Roselle, NJ (US); Thomas Schamper, Cranbury, NJ (US); Eddie Carl Henry, Flanders, NJ (US)

(73) Assignee: Coty S.A., Paris (FR)

( * ) Notice: Subject to any disclaimer, the term of this patent is extended or adjusted under 35 U.S.C. 154(b) by 185 days.

This patent is subject to a terminal disclaimer.

(21) Appl. No.: 11/951,993

(22) Filed: Dec. 6, 2007

(65) Prior Publication Data

US 2008/0131387 A1  Jun. 5, 2008

Related U.S. Application Data

(63) Continuation of application No. 11/157,472, filed on Jun. 21, 2005, now Pat. No. 7,341,713, which is a continuation-in-part of application No. 10/710,646, filed on Jul. 27, 2004, now Pat. No. 7,270,806.

(51) Int. Cl.
*A61Q 15/00* (2006.01)
*A61K 8/28* (2006.01)
*A61K 8/58* (2006.01)
*A61K 9/00* (2006.01)
*A61K 8/02* (2006.01)

(52) U.S. Cl. .............. 424/65; 424/66; 424/68; 424/400; 424/401

(58) Field of Classification Search .......... 424/65, 424/66, 68, 400, 401
See application file for complete search history.

(56) References Cited

U.S. PATENT DOCUMENTS

| | | | |
|---|---|---|---|
| 5,200,174 A * | 4/1993 | Gardlik et al. | 424/66 |
| 5,500,209 A * | 3/1996 | Mendolia et al. | 424/66 |
| 5,643,558 A | 7/1997 | Provancal et al. | |
| 5,871,720 A | 2/1999 | Gutierrez et al. | |
| 6,180,125 B1 | 1/2001 | Ortiz et al. | |
| 6,338,841 B1 | 1/2002 | Mattai et al. | |
| 6,668,641 B2 | 12/2003 | Ambrosina et al. | |
| 7,270,806 B2 | 9/2007 | Esposito et al. | |
| 7,341,713 B2 | 3/2008 | Esposito et al. | |
| 2002/0048557 A1 | 4/2002 | Cai et al. | |
| 2003/0211060 A1* | 11/2003 | Yin et al. | 424/66 |
| 2006/0024252 A1 | 2/2006 | Esposito et al. | |
| 2006/0073108 A1 | 4/2006 | Esposito et al. | |

FOREIGN PATENT DOCUMENTS

| | | |
|---|---|---|
| WO | WO-2006014962 A2 | 2/2006 |
| WO | WO-2006014962 A3 | 2/2006 |
| WO | WO-2007002197 A2 | 1/2007 |
| WO | WO-2007002197 A3 | 1/2007 |

OTHER PUBLICATIONS

"International Search Report and Written Opinion for Application No. PCT/US05/26502, date mailed Jul. 27, 2005", 8 pgs.
"Non-final office action mailed Sep. 25, 2006 in U.S. Appl. No. 11/157,472", 10 pgs.
"Notice of Allowance Mailed Oct. 29, 2007 in U.S. Appl. No. 11/157,472", 5 pgs.
"Notice of Allowance mailed Jul. 25, 2007 in U.S. Appl. No. 11/157,472", 4 pgs.
"PCT Application No. PCT/US06/24145, International Search Report mailed Aug. 29, 2007", 2 pgs.
"PCT Application No. PCT/US06/24145, Written Opinion mailed Aug. 29, 2007", 7 pgs.
"Response filed Jun. 21, 2005 to non-final office action mailed Sep. 25, 2006 in U.S. Appl. No. 11/157,472", 56 pgs.

* cited by examiner

*Primary Examiner*—Johann R Richter
*Assistant Examiner*—Luke E Karpinski
(74) *Attorney, Agent, or Firm*—Schwegman, Lundberg & Woessner, P.A.

(57) ABSTRACT

One embodiment of the invention described herein includes a method for improving stability of an antiperspirant. The method includes preparing a blend that comprises dibenzylidene sorbitol; adding an antiperspirant active to the blend, to make an antiperspirant blend; and adding one or more alkaline earth silicate salts to the antiperspirant blend in a concentration effective for stabilizing the dibenzylidene sorbitol.

20 Claims, 5 Drawing Sheets

LIQUID STICK ANTIPERSPIRANT

RELATED APPLICATIONS

This application is a continuation under 37 C.F.R. 1.53(b) of U.S. patent application Ser. No. 11/157,472 filed Jun. 21, 2005 now U.S. Pat. No. 7,341,713, which is a continuation-in-part of U.S. patent application Ser. No. 10/710,646 filed Jul. 27, 2004 (now U.S. Pat. No. 7,270,806), which applications are incorporated herein by reference and made a part hereof.

FIELD OF THE INVENTION

Embodiments of the invention relate to a stick antiperspirant, and to a method for making the stick antiperspirant.

BACKGROUND OF THE INVENTION

Antiperspirants have as a principle function, a requirement to eliminate adverse effects of perspiration. Antiperspirant function has frequently been associated with undesirable side effects. One undesirable side effect has been stickiness. Dimethicone and other silicones have been added to reduce tack, hence stickiness, in antiperspirants, as described in U.S. Pat. No. 6,180,125 and U.S. Patent Appln. Publ. No. 20020048557. Solutions to stickiness have, however, produced problems of instability in the antiperspirant formulations.

Dibenzylidene sorbitol (DBS) has been used as a gellant for clear cosmetic products since the 1970's. This gellant has been used to create clear antiperspirant sticks. One problem with the clear antiperspirant sticks stems from aluminum active salt dissolved in propylene glycol, which is a feature of the clear antiperspirant sticks. This feature gives the antiperspirant sticks a very sticky feel. Furthermore, the DBS gelled antiperspirant products are inherently unstable because DBS is an acetal. Acetals are not stable in an acid medium. The instability is due to the acidity of the antiperspirant salt.

DETAILED DESCRIPTION OF THE INVENTION

Figure 1:
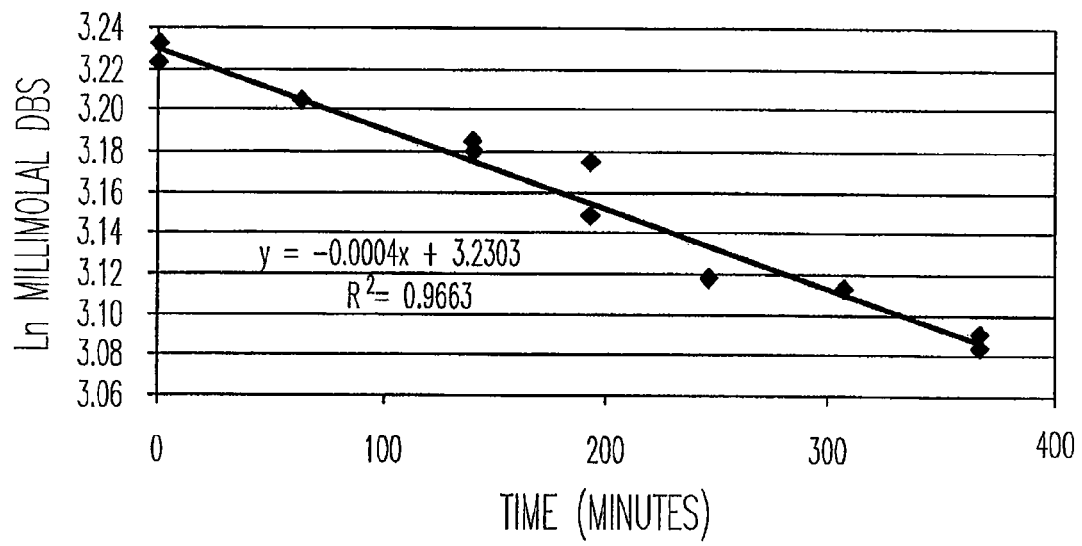
FIG. 1 is a graphical illustration of a degradation rate of an antiperspirant containing Dibenzylidene Sorbitol (DBS) and Zinc Glycinate.

One embodiment of the invention described herein includes a method for improving process stability and self stability of an antiperspirant product. The method includes preparing an antiperspirant blend that includes propylene glycol, dibenzylidene sorbitol (DBS), and adding an antiperspirant active material to the blend in a concentration effective for making an antiperspirant that provides antiperspirant protection to a user while improving shelf stability of the antiperspirant. The method also includes adding one or more alkaline earth silicate salt as a stabilizing agent. The alkaline earth silicate salts include one or more of sodium silicate, potassium silicate, calcium silicate, magnesium silicate, zinc silicate, aluminum silicate and mixtures thereof. The alkaline earth silicate salts are insoluble in water and propylene glycol.

It has been found that, for some embodiments, materials added to an antiperspirant formulation to impart stability, such as zinc glycinate, may be removed from the antiperspirant while maintaining the stability of the dibenzylidene sorbitol in the antiperspirant formulation. This removal is desirable for some embodiments because zinc glycinate has a tendency to discolor fragrance oils in the formulation.

Embodiments of the invention described herein generally deliver an opaque antiperspirant stick. However, a clear antiperspirant stick may be manufactured using process embodiments of the invention by maintaining refractive index of a continuous phase of the antiperspirant stick formulation within a narrow range.

For some embodiments, the process for making the opaque DBS antiperspirant stick is further stabilized using excess zinc glycinate. The addition of the alkaline earth silicate salts produces an antiperspirant having a longer shelf life stability than other conventional dibenzylidene sorbitol (DBS) gelled antiperspirants.

Another embodiment of the invention described herein includes an antiperspirant wherein the structurant, carrier, and antiperspirant consist essentially of propylene glycol, dibenzylidene sorbitol (DBS), solid active antiperspirant and one or more alkaline earth silicate salts as a stabilizing agent for increasing shelf life of the antiperspirant product. The salts include one or more of sodium silicate, potassium silicate, calcium silicate, magnesium silicate, zinc silicate, aluminum silicate and mixtures thereof. The alkaline earth silicate salts are insoluble in water and propylene glycol.

One other embodiment of the invention includes an antiperspirant consisting essentially of propylene glycol, dibenzylidene sorbitol, solid active antiperspirant, and one or more alkaline earth silicate salts as a stabilizing agent. The salts include one or more of sodium silicate, potassium silicate, calcium silicate, magnesium silicate, zinc silicate, aluminum silicate and mixtures thereof. The silicates are insoluble in water and propylene glycol, dibenzylidene sorbitol. The antiperspirant also includes hydroxylpropyl cellulose.

Another embodiment of the invention includes an antiperspirant consisting essentially of propylene glycol, dibenzylidene sorbitol (DBS), solid active antiperspirant, and one or more alkaline earth silicate salts as a stabilizing agent. The alkaline earth silicate salts include sodium silicate, potassium silicate, calcium silicate, magnesium silicate, zinc silicate, aluminum silicate and mixtures thereof. The silicates are insoluble in water, and stearyl alcohol.

One other embodiment includes an antiperspirant comprising a structurant, carrier, fragrance and antiperspirant, wherein the structurant, carrier, fragrance and antiperspirant consist essentially of propylene glycol, dibenzylidene sorbitol, solid active antiperspirant, and fragrance. The antiperspirant also includes one or more alkaline earth silicate salt as a stabilizing agent. The alkaline earth silicate salts include sodium silicate, potassium silicate, calcium silicate, magnesium silicate, zinc silicate, aluminum silicate and mixtures thereof. The alkaline earth silicate salts are insoluble in water.

Another embodiment includes an antiperspirant consisting essentially of propylene glycol, dibenzylidene sorbitol, solid active antiperspirant, hydroxypropyl cellulose, and one or more alkaline earth silicate salts as a stabilizing agent. The salts include sodium silicate, potassium silicate, calcium silicate, magnesium silicate, zinc silicate, aluminum silicate and mixtures thereof. The silicates are insoluble in water and stearyl alcohol.

One additional embodiment of the invention described herein includes a method for improving process stability of an antiperspirant comprising providing dibenzylidene sorbitol and a solid active antiperspirant to make the antiperspirant and adding one or more alkaline earth silicate salts as a stabilizing agent. The salts include Sodium Silicate, Potassium Silicate, calcium silicate, magnesium silicate, zinc silicate, aluminum silicate and mixtures thereof. The silicates are insoluble in water.

One embodiment of the invention described herein is an antiperspirant that includes a propylene glycol carrier in a concentration of 65 to 90 percent by weight; hydroxypropyl cellulose in a concentration of zero to 1.0 percent by weight; a structurant that includes dibenzylidene sorbitol (DBS) in a concentration of 0.5 to 3.0 percent by weight; an antiperspirant active material that includes solids in a concentration of 5 to 25 percent by weight and fragrance in a concentration of zero to 3 percent by weight. The formulation also includes one or more alkaline earth silicate salt as a stabilizing agent. The salts include sodium silicate, potassium silicate, calcium silicate, magnesium silicate, zinc silicate, aluminum silicate and mixtures thereof. The alkaline earth silicate salts are insoluble in water.

The formulation embodiments of the invention described herein produce an antiperspirant having low tack and process stability. While zinc glycinate is described for some embodiments, it has been found that zinc glycinate is not a required component of antiperspirants described herein.

The stability and low tack features of antiperspirant embodiments of the invention described herein are surprising because formulations containing dibenzylidene sorbitol (DBS) have heretofore been characterized as being sticky and susceptible to degradation of the dibenzylidene sorbitol. These prior art formulations have typically included emollients, dimethicone or other type of silicone in order to reduce tackiness. Antiperspirant embodiments described herein are stable and substantially low tack without including these tackiness reducing materials.

Embodiments of the invention described herein remedy the problems of low tack and instability by preparing a formulation wherein solid, suspended antiperspirant active ingredients are added to a formulation containing DBS, instead of a solution of antiperspirant salts described herein. Additionally, some method embodiments of the invention include adding a salt of an amino acid, which is effective for buffering the degradative acid hydrolysis of the dibenzylidene sorbitol. The amino acid salt or salts are added in addition to the alkaline earth salts.

The solid particulate antiperspirant amino acid salt slows the degradation of the dibenzylidene sorbitol, as compared to degradation of DBS by soluble antiperspirant actives employed in prior art clear antiperspirant sticks. Some of the formulation embodiments described herein do not require the presence of dimethicone or other silicone type to reduce tackiness because of the presence of the amino acid salt.

Some of the antiperspirant embodiments described herein have low tack and are stable because of the use of solid antiperspirant active material such as aluminum zirconium tetrachlorhydrex glycine complex, along with zinc glycinate solid powder that buffers the acidity of the antiperspirant salt. Combination with the dibenzylidene sorbitol structurant having a concentration of about 0.5 to 3.0% by weight creates an antiperspirant suspension that degrades much more slowly than soluble active antiperspirants. A propylene glycol concentration of 65 to 90% by weight disperses and dissolves the structurant at elevated temperatures to formulate an antiperspirant product having improved stability over conventional antiperspirants containing dibenzylidene sorbitol.

The term "structurant" as used herein refers to an additive used to suspend particles, and to thicken a suspension or to form solid gels. Dibenzylidene sorbitol, hydroxypropylcellulose and stearyl alcohol are structurants.

Solid active antiperspirants suitable for use in embodiments of the invention described herein include aluminum zirconium tetrachlorhydrex glycine complex with zinc glycinate and aluminum zirconium tetrachlorhydrex glycine complex with a salt other than zinc glycinate such as sodium glycinate and other water soluble amino acid salts such as sodium arginate. Other active solid antiperspirants include aluminum chlorhydrate, aluminum sesquichhlorhydrate, aluminum zirconium trichlorohydrex glycine, aluminum zirconium pentachlorohydrex glycine, aluminum zirconium tetrachlorohydrex glycine and aluminum zirconium octochlorohydrex glycine. The aluminum zirconium-containing materials are commonly referred to as antiperspirant active aluminum zirconium salts. Generally, the foregoing metal antiperspirant active materials are antiperspirant active metal salts listed in the Federal Register, Vol. 68, No. 110/Monday, Jun. 9, 2003/Rules and Regulations.

Fragrances suitable for use in embodiments of the invention described herein include natural products such as essential oils, flower oils, natural extracts from resins, gums, balsams, beans, mosses and other plants, and animal products such as ambergris and musk, as well as synthetic aromatic materials. It is believed that any fragrance material is suitable for use in the invention described herein. Suffice it to say that the fragrance materials generally fall into several well known categories, such as floral, spicy, woody, mossy, oriental, herbal, leather-tobacco and aldehydic groups. Men's fragrances suitable for use in the invention are classified into citrus, spice, leather, lavender, woody groups. Typically, fragrance materials are supplied as concentrates which generally contain up to about 3 percent fragrance by weight. Fragrance is optional and formulation embodiments of the invention described herein are not required to include a fragrance.

The hydroxypropyl cellulose is added as a structurant. Hydroxypropyl cellulose, when present in antiperspirant formulation embodiments, is present in concentrations of up to 1.0%. One problem with using DBS as the only structurant in a gelled stick is that the resulting product displays excessive syneresis, the weeping of liquid from the gelled solid. This syneresis is due to a low viscosity of the continuous liquid phase of the gel. The liquid seeps from the solid because of the capillary action. The hydroxyl propyl cellulose increases the viscosity of the liquid phase and dramatically decreases the syneresis.

Stabilizers suitable for use in some formulation embodiments of the invention include particulate organic or inorganic materials which are dispersible or dissolvable in the formulation. Other stabilizers usable for some formulations in the invention described herein include silica, mineral pigments, organic pigments, crosslinked polymers and copolymers of acrylic acid, cellulose ethers and mixtures thereof. Other stabilizers suitable for use include silica and mineral pigments. Examples of mineral pigments include, but are not limited to calcium carbonate, titanium dioxide, clay, organophilic clay, talc and gypsum. Cellulose ethers suitable for use as stabilizers include carboxymethyl cellulose and hydroxypropyl cellulose.

One formulation embodiment also includes stearyl alcohol as a structural component. Formulations that include stearyl alcohol have stearyl alcohol concentrations up to about 15% by weight.

Other materials suitable for use in embodiments of the invention, that impart structure, include organic structurants that are non-polymeric or polymeric. Non-polymeric structurants, including waxes and gellants, are often selected from fatty acids or salts thereof, often containing from 12 to 30 carbons such as stearic acid or sodium stearate, and/or fatty alcohols (typically insoluble in water) often containing from 12 to 30 carbons. The term "fatty" as used herein refers to a long chain aliphatic group, such as at least 8 or 12 linear carbons, which is frequently not branched (linear) and is typically saturated, but which may alternatively be branched and/or unsaturated. It is possible for the fatty acid to contain a hydroxyl group, as in 12-hydroxystearic acid, for example, as part of a gellant combination, and to employ amido or ester derivatives thereof. Examples of suitable higher molecular weight alcohols include behenyl alcohol and sterols such as lanosterol.

The dibenzylidene sorbitol also functions as a structurant and acts in combination with other structurants in the formulation, such as stearyl alcohol, for some embodiments. These structurants are believed to operate by interactions which are permanent unless disrupted by shear or heating. These structurants form a network of strands or fibers extending throughout a gelled liquid antiperspirant. In some cases, the fibers are observable by electron microscopy, although in other cases the observation of the fibers which are believed to be present is prevented by practical difficulties in preparing a suitable specimen. When observed, the primary fibers in a gel are generally thin (diameter less than 0.5μ, often less than 0.2μ) and appear to have numerous branches or interconnections. Primary fibers may entwine to form a thicker strand.

For some embodiments, fibers are crystalline. If the fibers are crystalline, they may or may not be the same polymorph as macroscopic crystals obtained by conventional crystallization from a solvent.

One liquid carrier material used in the present invention is propylene glycol. Other suitable liquid carriers include organic solvents. Suitable organic solvents have a melting point of less than about 10° C., such as less than 5° C. This melting point range benefits both low temperature storage stability and ease of manufacture. A class of organic solvents suitable for use in the invention described herein are aliphatic alcohols (monohydric or polyhydric, preferably having 2 to 8 carbon atoms) and polyglycol ethers, preferably oligoglycol ethers having only 2 to 5 repeat units. Examples include dipropylene glycol, glycerol propylene glycol, butylene glycol, ethanol, propanol, isopropanol, and industrial methylated spirits. Suitable organic solvents include aliphatic alcohols, in particular those having 2 to 3 carbon atoms, especially ethanol and isopropanol.

Mixtures of carrier materials are also usable. The total amount of carrier material employed is for some embodiments, from 30% to 99%, and for other embodiments, from 60% to 98%, expressed as a weight percentage of the total weight of the composition.

The formulation of the invention described herein is made, for one embodiment, by adding hydroxypropyl cellulose to propylene glycol and blending to make a solution. The dibenzylidene sorbitol is added to the solution to gel the solution and to act as a structurant, forming a network of fibers within the solution. Stearyl alcohol is added for some embodiments and also acts as a structurant. The aluminum zirconium tetrachlorhydrex glycine complex with zinc glycinate is then added to make a final antiperspirant product mixture.

The final antiperspirant product mixture is added to a packaging that is capable of shaping and holding a stick. In one embodiment, the packaging is polymeric. The antiperspirant mixture takes the shape of the container. The container is labeled with indicia branding the antiperspirant mixture and providing other information such as, for example, ingredients.

One DBS gelled antiperspirant stick is made using the following formulation:

Example 1

DBS Gelled Antiperspirant Stick

| Ingredient | % weight/weight |
| --- | --- |
| Propylene Glycol | 75.7 |
| Hydroxypropylcellulose | 0.3 |
| Dibenzylidene Sorbitol | 1.0 |
| Stearyl alcohol | 3.0 |
| Aluminum Zirconium trichlorhydrex glycine (powder) | 18.0 |
| Zinc Glycinate | 2.0 |

The formulation in Example 1 is made using the following procedure:

Manufacturing Process of Example 1

1) The Propylene Glycol, Hydroxypropylcellulose, and dibenzylidene sorbitol were mixed to form a mixture, into an appropriately sized vessel for heating.

2) The mixture was heated with constant stirring to 95° C. The temperature was maintained until the mixture formed a solution that was clear and all of the material was dissolved.

3) The heat was reduced and stearyl alcohol was added to the heated mixture. The temperature was lowered to 80° C.

4) Aluminum/zirconium tetrachlorhydrex glycine powder was added to the mixture.

5) Zinc Glycinate was added to the mixture.

6) The liquid mixture was poured into antiperspirant stick containers when the temperature was between 70° C. and 75° C.

7) The product was allowed to cool and solidify. Once cool it was used as an antiperspirant product.

The formula of Example 1 was used to measure the kinetic degradation of the Dibenzylidene sorbitol into Sorbitol, Benzaldehyde and propylene glycol—Benzaldehyde Acetal. The reaction rate of the degradation was monitored by measuring the DBS remaining in the formula after heating at 75° C. for six hours. See FIG. 1.

Figure 2:
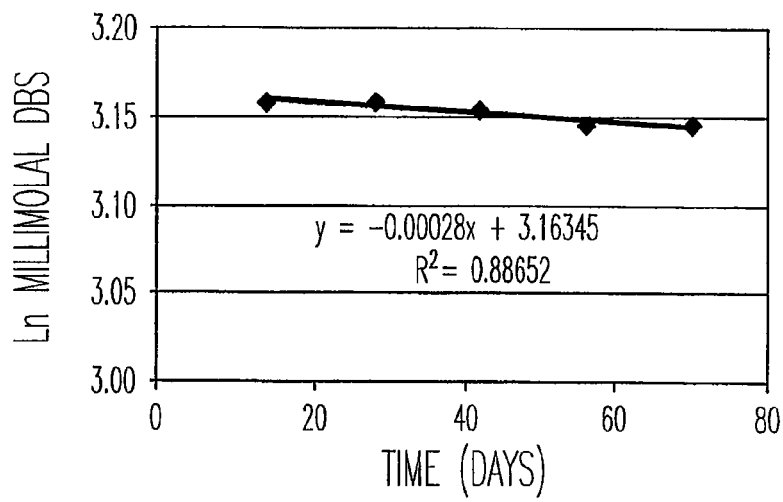
FIG. 2 is a graphical illustration of a degradation rate of an antiperspirant containing DBS and Calcium Silicate at room temperature.
Figure 3:
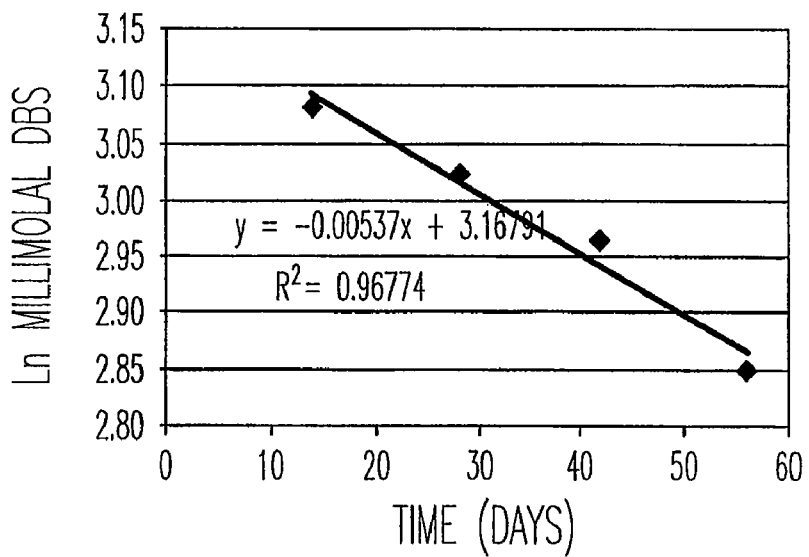
FIG. 3 is a graphical illustration of a degradation rate of an antiperspirant containing DBS and Calcium Silicate at 45 degrees Centigrade.

Antiperspirant sticks having a size of about 1.6 oz., which were poured from the formula of Example 1 at an initial time point, were stored at room temperature in a first test and at 45° C. in a second test. The antiperspirant sticks were removed from room temperature storage at the end of two weeks and were stored in a freezer until the end of eight weeks. At the end of eight weeks, the sticks were analyzed for the conversion of Dibenzylidene sorbitol into Sorbitol, Benzaldehyde and the propylene glycol—Benzaldehyde Acetal. Results are shown in FIGS. 2 and 3. Data used to prepare the figures is as follows:

DBS Degradation in Stick Formulation of Example 1 C@Room Temp

| Time (days) | % | DBS (g/KG) | DBS (mMoles/Kg) | Ln m[DBS] |
|---|---|---|---|---|
| 14 | 0.842 | 8.42 | 23.52 | 3.16 |
| 28 | 0.842 | 8.42 | 23.52 | 3.16 |
| 42 | 0.838 | 8.38 | 23.41 | 3.15 |
| 56 | 0.831 | 8.31 | 23.21 | 3.14 |
| 70 | 0.831 | 8.31 | 23.21 | 3.14 |

DBS Degradation in Stick Made from the Formulation of Example 1 C@45°

| Time (days) | % | DBS (g/KG) | DBS (mMoles/Kg) | Ln m[DBS] |
|---|---|---|---|---|
| 14 | 0.78 | 7.8 | 21.79 | 3.08 |
| 28 | 0.736 | 7.36 | 20.56 | 3.02 |
| 42 | 0.694 | 6.94 | 19.39 | 2.96 |
| 56 | 0.619 | 6.19 | 17.29 | 2.85 |

The following examples described herein illustrate how the presence of calcium silicate in a formulation such as is described in Example 1 slowed the degradation of DBS in the presence of Aluminum/Zirconium active salts. FIGS. 6, 7, 8 and 9 for Example 2 illustrate that the rate constant for the DBS degradation reaction was lowered four-fold in process and nearly ten-fold for antiperspirant stick aging at 45° C., as compared to the rate constant for the formulation described in Example 1. As a consequence, the formulation of Example 2 is four-fold to ten-fold more stable than the formulation of Example 1. The formulation for Example 2 of an antiperspirant stick with calcium silicate is as follows:

Example 2

DBS Gelled Antiperspirant Stick with Calcium Silicate

| Ingredient | % weight/weight |
|---|---|
| Propylene Glycol | 78.53 |
| Hydroxypropylcellulose | 0.37 |
| Dibenzylidene Sorbitol | 1.1 |
| Stearyl alcohol | 3.0 |
| Calcium Silicate | 1.0 |
| Aluminum Zirconium tetrachlorhydrex glycine (powder) | 15.0 |
| Fragrance | 1.0 |

This formulation was manufactured as follows:

1) The Propylene Glycol, Hydroxypropylcellulose, and dibenzylidene sorbitol were mixed, forming a mixture, into an appropriately sized vessel for heating.

2) The mixture was heated with constant stirring to 95° C., forming a solution, and the temperature was maintained until the solution was clear and all of the material was dissolved.

3) The heat was lowered and stearyl alcohol was added. The temperature was lowered to 80° C.

4) Calcium Silicate was added and mixed into the batch.

5) Aluminum/zirconium tetrachlorhydrex glycine powder was added to the mixture.

6) Fragrance was added to the liquid mixture.

7) The liquid mixture was poured into antiperspirant stick containers when the temperature was between 70° C. and 75° C.

8) The product was allowed to cool and solidify. Once cooled, the product was usable as an antiperspirant product.

Determination of the Degradation Rate of DBS in the Presence Aluminum/Zirconium Active Salt at 75° C.

Figure 4:
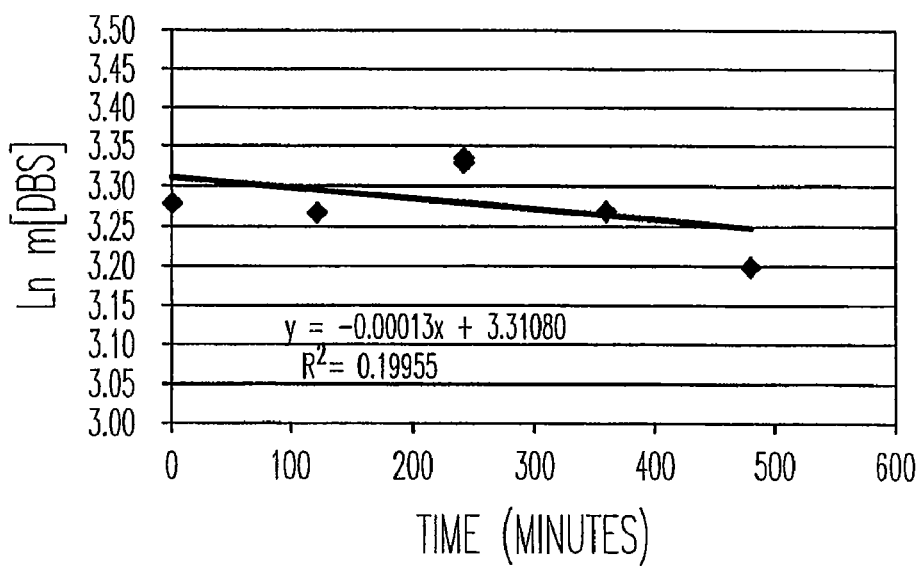
FIG. 4 is a graphical illustration of a degradation rate of a finished formula of an antiperspirant containing DBS and Calcium Silicate.

The formulation of Example 2 was used to measure the kinetic degradation of the Dibenzylidene sorbitol into Sorbitol, Benzaldehyde and the propylene glycol—Benzaldehyde Acetal. The reaction rate was monitored by measuring the DBS remaining in the formulation after heating at 75° C. for eight hours. The rate of DBS degradation is illustrated graphically in FIG. 4.

Figure 5:
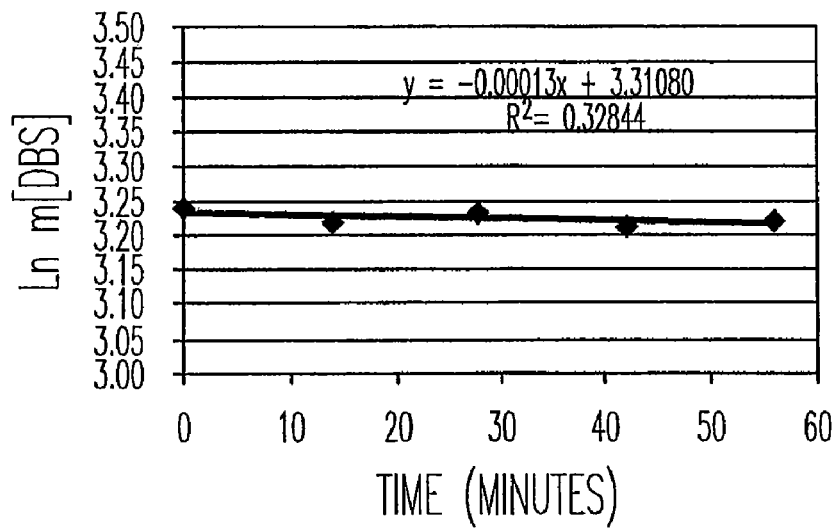
FIG. 5 is a graphical illustration of a degradation rate of a stick formula of an antiperspirant containing DBS and Calcium Silicate at room temperature for eight weeks.
Figure 6:
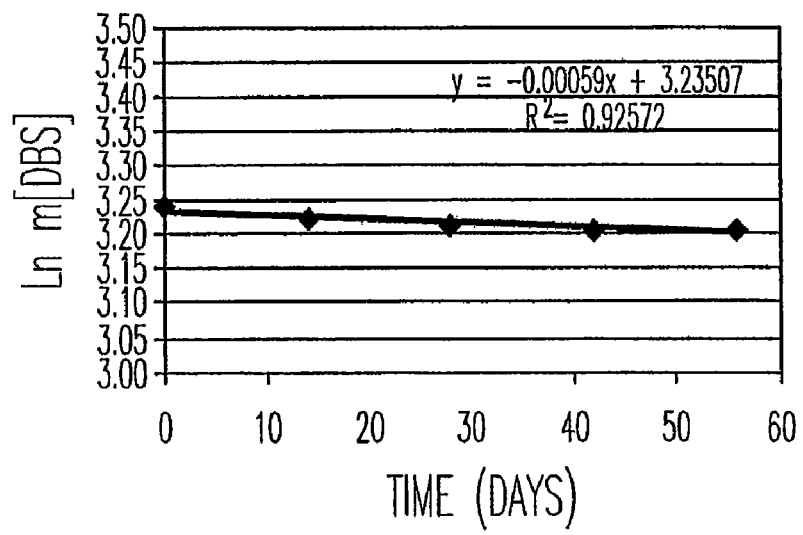
FIG. 6 is a graphical illustration of a degradation rate of a stick formula of an antiperspirant containing DBS and Calcium Silicate at 45 degrees Centigrade for eight weeks.

The antiperspirant sticks, having a size of about 1.6 oz, were made using the formula of Example 2 and were poured and stored at room temperature at 45° C. The sticks were removed from the room temperature storage at the end of two weeks and were stored in a freezer until the end of eight weeks. At the end of eight weeks the sticks were analyzed for the presence of Dibenzylidene sorbitol degradation into Sorbitol, Benzaldehyde and the propylene glycol—Benzaldehyde Acetal. Results are shown in FIG. 5 for storage at room temperature for eight weeks, and in FIG. 6, for storage at 45° C. for eight weeks.

DBS Degradation with the Formulation of Example 2

Finished Formula

| Time | % | DBS (g/KG) | DBS (mMoles/Kg) | Ln m[DBS] |
|---|---|---|---|---|
| 0 | 0.949 | 9.49 | 26.51 | 3.28 |
| 120 | 0.94 | 9.4 | 26.26 | 3.27 |
| 240 | 1.005 | 10.05 | 28.07 | 3.33 |
| 240 | 0.998 | 9.98 | 27.88 | 3.33 |
| 360 | 0.943 | 9.43 | 26.34 | 3.27 |
| 480 | 0.876 | 8.76 | 24.47 | 3.20 |

DBS Degradation in Stick with the Formulation of Example 2@room temp

| Time (days) | % | DBS (g/KG) | DBS (mMoles/Kg) | Ln m[DBS] |
|---|---|---|---|---|
| 0 | 0.913 | 9.13 | 25.50 | 3.24 |
| 14 | 0.894 | 8.94 | 24.97 | 3.22 |
| 28 | 0.909 | 9.09 | 25.39 | 3.23 |
| 42 | 0.889 | 8.89 | 24.83 | 3.21 |
| 56 | 0.897 | 8.97 | 25.06 | 3.22 |

DBS Degradation in Stick with the Formulation of Example 2@45°

| Time (days) | % | DBS (g/KG) | DBS (mMoles/Kg) | Ln m[DBS] |
|---|---|---|---|---|
| 0 | 0.913 | 9.13 | 25.50 | 3.24 |
| 14 | 0.901 | 9.01 | 25.17 | 3.23 |
| 28 | 0.89 | 8.9 | 24.86 | 3.21 |
| 42 | 0.887 | 8.87 | 24.78 | 3.21 |
| 56 | 0.883 | 8.83 | 24.66 | 3.21 |

This next set of examples further illustrate a use of calcium silicate to stabilize DBS in the processing of an antiperspirant stick. The following exemplary formulations were capable of delivering a clear DBS antiperspirant stick provided the Refractive Index of the Calcium silicate was matched with the continuous liquid phase of the stick. The formulation of Example 3 is as follows:

Example 3

DBS Gelled Antiperspirant Stick using Soluble Al/Zr Active

| Ingredient | % weight/weight |
|---|---|
| Propylene Glycol | 44.5 |
| Hydroxypropylcellulose | 0.4 |
| Dibenzylidene Sorbitol | 1.1 |
| Stearyl alcohol | 3.0 |
| 30% Aluminum Zirconium tetrachlorhydrex glycine (pg) | 50.0 |
| Fragrance | 1.0 |

Example 4

DBS Gelled Antiperspirant Stick Using Soluble Al/Zr Active with Zinc Glycinate

| Ingredient | % weight/weight |
|---|---|
| Propylene Glycol | 43.9 |
| Hydroxypropylcellulose | 0.4 |
| Dibenzylidene Sorbitol | 1.7 |
| Stearyl alcohol | 3.0 |
| 30% Aluminum Zirconium trichlorhydrex glycine with Zinc Glycinate (pg) | 50.0 |
| Fragrance | 1.0 |

Example 5

DBS Gelled Antiperspirant Stick Using Soluble Al/Zr Active with Calcium Silicate

| Ingredient | % weight/weight |
|---|---|
| Propylene Glycol | 43.5 |
| Hydroxypropylcellulose | 0.4 |
| Dibenzylidene Sorbitol | 1.1 |
| Stearyl alcohol | 3.0 |
| Calcium Silicate | 1.0 |
| 30% Aluminum Zirconium tetrachlorhydrex glycine (pg) | 50.0 |
| Fragrance | 1.0 |

Determination of the Degradation Rate of DBS in the Presence Aluminum/Zirconium Active Salt at 75° C.

The formulas of Examples 3 and 4 were used to measure the kinetic degradation of the Dibenzylidene sorbitol into Sorbitol, Benzaldehyde and the propylene glycol—Benzaldehyde Acetal. The reaction rate was monitored by measuring the DBS remaining in the formula after heating at 75° C. for two hours. See FIGS. 7,8, and 9.

Figure 7:
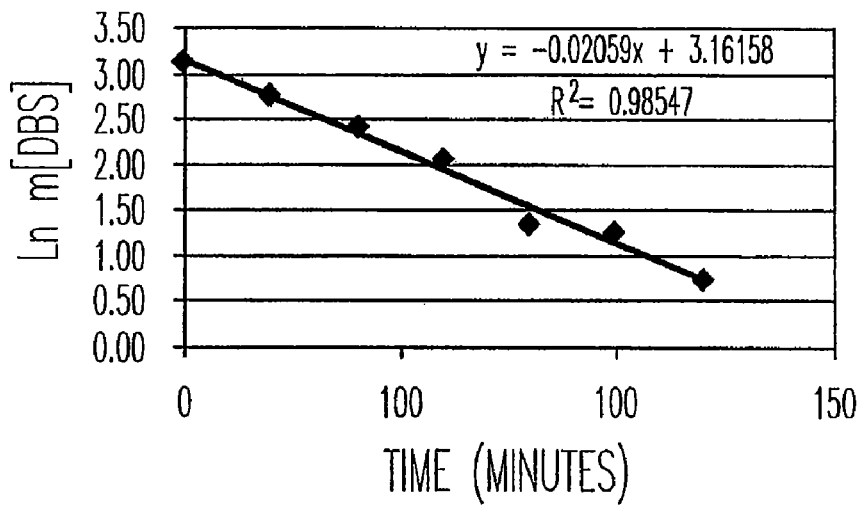
FIG. 7 is a graphical view of DBS degradation into Sorbitol, Benzaldehyde and the propylene glycol—Benzaldehyde Acetal.
Figure 8:
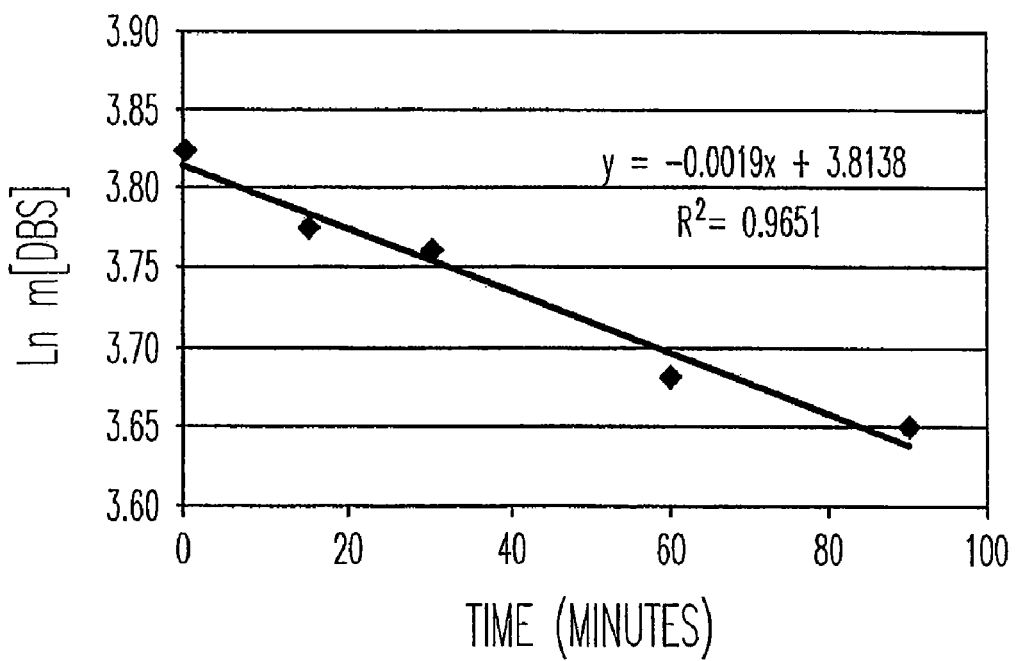
FIG. 8 is a graphical view of DBS degradation with 15% aluminum zirconium tetrachlorohydrex with zinc glycinate.
Figure 9:
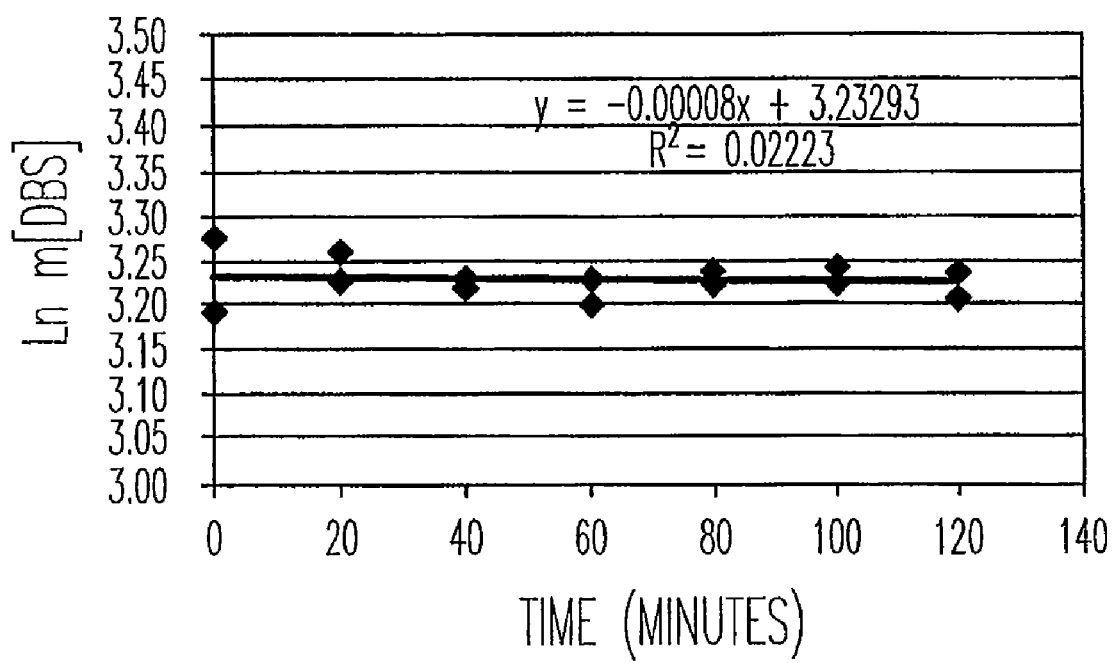
FIG. 9 is a graphical view of DBS degradation with 15% aluminum zirconium tetrachlorohydrex with calcium silicate.

Inspection of FIGS. 7, 8 and 9 shows that the rate constant for the DBS degradation was lowered about ten fold for the Zinc glycinate additive and an amazing 4000 fold for the Calcium Silicate.

DBS Degradation with 15% Reach AZP-908 (pg 30)

| Time | % | DBS (g/KG) | DBS (mMoles/Kg) | Ln m[DBS] |
|---|---|---|---|---|
| 0 | 0.828 | 8.28 | 23.13 | 3.14 |
| 20 | 0.554 | 5.54 | 15.47 | 2.74 |
| 40 | 0.395 | 3.95 | 11.03 | 2.40 |
| 60 | 0.267 | 2.67 | 7.46 | 2.01 |
| 80 | 0.131 | 1.31 | 3.66 | 1.30 |
| 100 | 0.12 | 1.2 | 3.35 | 1.21 |
| 120 | 0.071 | 0.71 | 1.98 | 0.68 |

DBS Degradation Aluminum zirconium Trichlorhydex Gly with Zn Glycinate Westchlor Lot 33901-z

| Time (min) | % DBS | DBS (g/KG) | DBS (mMoles/Kg) | Ln m[DBS] |
|---|---|---|---|---|
| 0 | 1.64 | 16.4 | 45.81 | 3.82 |
| 15 | 1.56 | 15.6 | 43.58 | 3.77 |
| 30 | 1.54 | 15.4 | 43.02 | 3.76 |
| 60 | 1.42 | 14.2 | 39.66 | 3.68 |
| 90 | 1.38 | 13.8 | 38.55 | 3.65 |

DBS Degradation with 15% Reach AZP-908 (pg 30) with Calcium Silicate

| Time | % | DBS (g/KG) | DBS (mMoles/Kg) | Ln m[DBS] |
|---|---|---|---|---|
| 0 | 0.947 | 9.47 | 26.45 | 3.28 |
| 0 | 0.871 | 8.71 | 24.33 | 3.19 |
| 20 | 0.931 | 9.31 | 26.01 | 3.26 |
| 20 | 0.901 | 9.01 | 25.17 | 3.23 |
| 40 | 0.904 | 9.04 | 25.25 | 3.23 |
| 40 | 0.894 | 8.94 | 24.97 | 3.22 |
| 60 | 0.903 | 9.03 | 25.22 | 3.23 |
| 60 | 0.876 | 8.76 | 24.47 | 3.20 |
| 80 | 0.914 | 9.14 | 25.53 | 3.24 |
| 80 | 0.897 | 8.97 | 25.06 | 3.22 |
| 100 | 0.915 | 9.15 | 25.56 | 3.24 |
| 100 | 0.901 | 9.01 | 25.17 | 3.23 |
| 120 | 0.91 | 9.1 | 25.42 | 3.24 |
| 120 | 0.886 | 8.86 | 24.75 | 3.21 |

DBS Degradation Westwood Active Formula #UA21-23R

| Time (min) | % | DBS (g/KG) | DBS (mMoles/Kg) | Ln m[DBS] | Benz (mg/kg) | Benz (mMoles/kg) | Ln [benz] |
|---|---|---|---|---|---|---|---|
| 0 | 0.907 | 9.07 | 25.34 | 3.23 | 6.8 | 0.06 | −2.75 |
| 0 | 0.899 | 8.99 | 25.11 | 3.22 | | | |
| 63 | 0.882 | 8.82 | 24.64 | 3.20 | 11.38 | 0.11 | −2.23 |
| 63 | 0.882 | 8.82 | 24.64 | 3.20 | 11.47 | 0.11 | −2.22 |
| 140 | 0.865 | 8.65 | 24.16 | 3.18 | 19.23 | 0.18 | −1.71 |
| 140 | 0.861 | 8.61 | 24.05 | 3.18 | 19.13 | 0.18 | −1.71 |
| 193 | 0.856 | 8.56 | 23.91 | 3.17 | 24.23 | 0.23 | −1.48 |
| 193 | 0.834 | 8.34 | 23.30 | 3.15 | 23.28 | 0.22 | −1.52 |
| 247 | 0.809 | 8.09 | 22.60 | 3.12 | 28.61 | 0.27 | −1.31 |
| 247 | 0.809 | 8.09 | 22.60 | 3.12 | 28.31 | 0.27 | −1.32 |
| 307 | 0.804 | 8.04 | 22.46 | 3.11 | 34.55 | 0.33 | −1.12 |
| 307 | 0.805 | 8.05 | 22.49 | 3.11 | 34.36 | 0.32 | −1.13 |
| 368 | 0.787 | 7.87 | 21.98 | 3.09 | 40.18 | 0.38 | −0.97 |
| 368 | 0.782 | 7.82 | 21.84 | 3.08 | 39.7 | 0.37 | −0.98 |

Although the invention has been described with reference to specific forms thereof, it will be understood that many changes and modifications may be made without departing from the spirit of this invention.

What is claimed:

1. A method for improving stability of an antiperspirant free of zinc glycinate, comprising:
   preparing a blend free of zinc glycinate, the blend consisting of dibenzylidene sorbitol
      a liquid carrier consisting of one or more of the solvents selected from the group consisting of propylene glycol, an aliphatic alcohol, and a polyglycol ether; and
      optionally, hydroxypropyl cellulose or stearyl alcohol;
   wherein the blend is devoid of any other solvents;
   adding an antiperspirant active to the blend, to make an antiperspirant blend; and
   adding sodium silicate, potassium silicate, calcium silicate, magnesium silicate, zinc silicate, aluminum silicate, or mixtures thereof to the antiperspirant blend in a concentration effective for stabilizing the dibenzylidene sorbitol to form a stabilized antiperspirant blend.

2. The method of claim 1 wherein the sodium silicate, potassium silicate, calcium silicate, magnesium silicate, zinc silicate, aluminum silicate, or mixtures thereof stabilizes the dibenzylidene sorbitol for process temperatures up to 105° C.

3. The method of claim 1 further comprising adding the antiperspirant to a container.

4. The method of claim 1 further comprising adding hydroxypropyl cellulose to the blend.

5. The method of claim 1 further comprising adding stearyl alcohol to the blend.

6. The method of claim 1 further comprising adding fragrance to the antiperspirant blend.

7. The method of claim 1 wherein the antiperspirant active comprises aluminum zirconium tetrachlorhydrex glycine complex.

8. A product made by the process of claim 1.

9. An antiperspirant free of zinc glycinate, comprising:
   a liquid carrier consisting of one or more solvents selected from the group consisting of propylene glycol, an aliphatic alcohol, and a polyglycol ether;
   dibenzylidene sorbitol;
   sodium silicate, potassium silicate, calcium silicate, magnesium silicate, zinc silicate, aluminum silicate, or mixtures thereof in a concentration effective for stabilizing the dibenzylidene sorbitol; and optionally, hydroxypropyl cellulose or stearyl alcohol or a mixture of hydroxypropyl cellulose or stearyl alcohol;

wherein the antiperspirant is devoid of any other solvents.

10. The antiperspirant of claim 9 wherein the propylene glycol concentration is within a range of about 65 to 90% w/w.

11. The antiperspirant of claim 9 wherein the dibenzylidene sorbitol concentration is within a range of about 0.5 to 3.0% w/w.

12. The antiperspirant of claim 9 further comprising aluminum zirconium tetrachlorohydrex glycine complex.

13. An antiperspirant, comprising:
a liquid carrier consisting of one or more solvents selected from the group consisting of propylene glycol, an aliphatic alcohol, and a polyglycol ether;
dibenzylidene sorbitol;
sodium silicate, potassium silicate, calcium silicate, magnesium silicate, zinc silicate, aluminum silicate, or mixtures thereof in a concentration effective for stabilizing the dibenzylidene sorbitol; and
optionally, hydroxypropyl cellulose or stearyl alcohol or a mixture of hydroxypropyl cellulose or stearyl alcohol,
wherein the antiperspirant is devoid of any other solvents.

14. The method of claim 1, wherein the concentration of sodium silicate, potassium silicate, calcium silicate, magnesium silicate, zinc silicate, aluminum silicate, or mixtures thereof in the stabilized antiperspirant blend is 1% w/w.

15. The method of claim 1, wherein the concentration of sodium silicate, potassium silicate, calcium silicate, magnesium silicate, zinc silicate, aluminum silicate, or mixtures thereof in the stabilized antiperspirant blend is an amount that increases the stability of the dibenzylidene sorbitol relative to the stability of dibenzylidene sorbitol in an unstabilized antiperspirant, wherein the unstabilized antiperspirant is devoid of sodium silicate, potassium silicate, calcium silicate, magnesium silicate, zinc silicate, aluminum silicate, or mixtures thereof but otherwise has the same composition as the stabilized antiperspirant blend.

16. The antiperspirant of claim 9, wherein the concentration of sodium silicate, potassium silicate, calcium silicate, magnesium silicate, zinc silicate, aluminum silicate, or mixtures thereof is 1% w/w.

17. The antiperspirant of claim 9, wherein the concentration of sodium silicate, potassium silicate, calcium silicate, magnesium silicate, zinc silicate, aluminum silicate, or mixtures thereof is an amount that increases the stability of the dibenzylidene sorbitol relative to the stability of dibenzylidene sorbitol in an unstabilized antiperspirant, wherein the unstabilized antiperspirant is devoid of sodium silicate, potassium silicate, calcium silicate, magnesium silicate, zinc silicate, aluminum silicate, or mixtures thereof but otherwise has the same composition as the stabilized antiperspirant blend.

18. The antiperspirant of claim 9, further comprising a solid active antiperspirant.

19. The antiperspirant of claim 13, wherein the concentration of sodium silicate, potassium silicate, calcium silicate, magnesium silicate, zinc silicate, aluminum silicate, or mixtures thereof is 1% w/w.

20. The antiperspirant of claim 13, wherein the concentration of sodium silicate, potassium silicate, calcium silicate, magnesium silicate, zinc silicate, aluminum silicate, or mixtures thereof is an amount that increases the stability of the dibenzylidene sorbitol relative to the stability of dibenzylidene sorbitol in an unstabilized antiperspirant, wherein the unstabilized antiperspirant is devoid of sodium silicate, potassium silicate, calcium silicate, magnesium silicate, zinc silicate, aluminum silicate, or mixtures thereof but otherwise has the same composition as the stabilized antiperspirant blend.

* * * * *